(12) United States Patent
Lohse et al.

(10) Patent No.: US 7,605,267 B2
(45) Date of Patent: Oct. 20, 2009

(54) PROCESS FOR THE PREPARATION OF 5-(HALOCETYL)-8-(SUBSTITUTED OXY)-(1H)-QUINOLIN-2-ONES

(75) Inventors: Olivier Lohse, Rixheim (FR); Gerhard Penn, Oberwil (CH); Hanspeter Schilling, Bottmingen (CH)

(73) Assignee: Novartis AG, Basel (CH)

( * ) Notice: Subject to any disclaimer, the term of this patent is extended or adjusted under 35 U.S.C. 154(b) by 540 days.

(21) Appl. No.: 10/550,621

(22) PCT Filed: Apr. 1, 2004

(86) PCT No.: PCT/EP2004/003479

§ 371 (c)(1),
(2), (4) Date: Nov. 3, 2005

(87) PCT Pub. No.: WO2004/087668

PCT Pub. Date: Oct. 14, 2004

(65) Prior Publication Data

US 2006/0189653 A1      Aug. 24, 2006

Related U.S. Application Data

(60) Provisional application No. 60/459,724, filed on Apr. 2, 2003.

(51) Int. Cl.
*C07D 215/38* (2006.01)
(52) U.S. Cl. .................................................... 546/157
(58) Field of Classification Search .................. 546/157
See application file for complete search history.

(56) References Cited

U.S. PATENT DOCUMENTS 6,800,643 B2 * 10/2004 Cuenoud et al. ............ 514/312
6,878,721 B1 * 4/2005 Cuenoud et al. ............ 514/312

FOREIGN PATENT DOCUMENTS

| EP | 0 052 016 | 5/1982 |
|---|---|---|
| ES | 8 605 239 | 8/1986 |
| WO | 95/25104 | 9/1995 |
| WO | 00/75114 | 12/2000 |
| WO | 03/042160 | 5/2003 |

OTHER PUBLICATIONS

Milecki, J Med Chem, vol. 30, pp. 1563-1566, 1987.*
Amlaiky et al., "Derives Ethers D'Oximes a Noyau Carbostyrile. 4. Syntheses et Activities Beta- Bloquantes", European Journal of Medicinal Chemistry, vol. 19, No. 4, pp. 341-346 (1984).
Valkenberg et al., "Friedel-Crafts Acylation of Aromatics Catalysed by Supported Ionic Liquids", Applied Catalysis A: General, vol. 215 No. 1-2, pp. 185-190 (2001).

* cited by examiner

*Primary Examiner*—D. Margaret Seaman
(74) *Attorney, Agent, or Firm*—Cozette M McAvoy

(57) ABSTRACT

The invention relates to a process for preparing 5-(α-haloacetyl)-8-substituted oxy-(1H)-quinolin-2-ones. The process involves (i) reacting (a) 8-hydroxy-(1H)-quinolin-2-one with an acylating agent and a Lewis acid to form 5-acetyl-8-hydroxy-(1H)-quinolin-2-one; or (b) 8-hydroxy-(1H)-quinolin-2-one with an acylating agent to form 8-acetoxy-(1H)-quinolin-2-one, and treating, in-situ, the 8-acetoxy-(1H)-quinolin-2-one with a Lewis acid to form 5-acetyl-8-hydroxy-(1H)-quinolin-2-one; or (c) 8-acetoxy-(1H)-quinolin-2-one with a Lewis acid to form 5-acetyl-8-hydroxy-(1H)-quinolin-2-one; (ii) reacting the 5-acetyl-8-hydroxy-(1H)-quinolin-2-one prepared in Step (i) with a compound having the Formula RL in the presence of a base and a solvent to form 5-acetyl-8-substituted oxy-(1H)-quinolin-2-one, wherein R is a protecting group and L is a leaving group; and (iii) reacting the 5-acetyl-8-substituted oxy-(1H)-quinolin-2-one with a halogenating agent in the presence of a solvent to form a 5-(α-haloacetyl)-8-substituted oxy-(1H)-quinolin-2-one.

15 Claims, No Drawings

PROCESS FOR THE PREPARATION OF 5-(HALOCETYL)-8-(SUBSTITUTED OXY)-(1H)-QUINOLIN-2-ONES

This application claims benefit of U.S. Provisional Application No. 60/459,724, filed Apr. 2, 2003, which in its entirety is herein incorporated by reference.

The present invention provides a process for preparing 5-(α-haloacetyl)-8-benzyloxy-(1H)-quinolin-2-ones such as 5-(α-chloroacetyl)-8-benzyloxy-(1H)-quinolin-2-one, which are useful intermediates from which to prepare 5-[(R)-2-(5,6-diethyl-indan-2-ylamino)-1-hydroxy-ethyl]-8-hydroxy-(1H)-quinolinone-2-one salts.

5-[(R)-2-(5,6-Diethyl-indan-2-ylamino)-1-hydroxy-ethyl]-8-hydroxy-(1H)-quinolinone-2-one salts are β-selective adrenoceptor agonists with potent bronchodilator activity. For example, 5-[(R)-2-(5,6-diethyl-indan-2-ylamino)-1-hydroxy-ethyl]-8-hydroxy-(1H)-quinolinone-2-one maleate is especially useful for treating asthma and chronic obstructive pulmonary disease (COPD). In addition, the maleate salt has been shown to have a very long duration of action in vitro and in vivo.

In a first aspect the present invention provides a process for preparing 5-(α-haloacetyl)-8-substituted oxy-(1H)-quinolin-2-ones comprising:
(a) reacting
   (i) 8-hydroxy-(1H)-quinolin-2-one with an acylating agent and a Lewis acid to form 5-acetyl-8-hydroxy-(1H)-quinolin-2-one; or
   (ii) 8-hydroxy-(1H)-quinolin-2-one with an acylating agent to form 8-acetoxy-(1H)-quinolin-2-one, and treating, in-situ, the 8-acetoxy-(1H)-quinolin-2-one with a Lewis acid to form 5-acetyl-8-hydroxy-(1H)-quinolin-2-one; or
   (iii) 8-acetoxy-(1H)-quinolin-2-one with a Lewis acid to form 5-acetyl-8-hydroxy-(1H)-quinolin-2-one;
(b) reacting the 5-acetyl-8-hydroxy-(1H)-quinolin-2-one prepared in Step (a) with a compound having the Formula RL in the presence of a base and a solvent to form 5-acetyl-8-substituted oxy-(1H)-quinolin-2-one, wherein R is a protecting group and L is a leaving group; and
(c) reacting the 5-acetyl-8-substituted oxy-(1H)-quinolin-2-one with a halogenating agent in the presence of a solvent to form a 5-(α-haloacetyl)-8-substituted oxy-(1H)-quinolin-2-one.

This process provides the 5-(α-chloroacetyl)-8-benzyloxy-(1H)-quinolin-2-one in high selectivity and yield, and minimizes or eliminates the formation of regioisomers, such as 7-acetyl-8-benzyloxy-(1H)-quinolin-2-one-(1H).

In one embodiment of the invention, Step (a) preferably involves reacting 8-hydroxy-(1H)-quinolin-2-one with an acylating agent and a Lewis acid to form 5-acetyl-8-hydroxy-(1H)-quinolin-2-one.

In another embodiment of the invention, Step (a) preferably involves reacting 8-hydroxy-(1H)-quinolin-2-one with an acylating agent to form 8-acetoxy-(1H)-quinolin-2-one, and treating, in-situ, the 8-acetoxy-(1H)-quinolin-2-one with a Lewis acid to form 5-acetyl-8-hydroxy-(1H)-quinolin-2-one.

In a further embodiment of the invention, Step (a) preferably involves reacting 8-acetoxy-(1H)-quinolin-2-one with a Lewis acid to form 5-acetyl-8-hydroxy-(1H)-quinolin-2-one.

Terms used in the specification have the following meanings:

"Halo" or "halogen" as used herein denotes an element belonging to group 17 (formerly group VII) of the Periodic Table of Elements, which may be, for example, fluorine, chlorine, bromine or iodine. Preferably halo or halogen is chlorine, bromine or iodine.

"$C_1$-$C_{18}$-aliphatic group" as used herein denotes an aliphatic group having 1 to 18 carbon atoms. Preferably the $C_1$-$C_{18}$-aliphatic group is ethyl, propyl or butyl.

"$C_4$-$C_{18}$-aromatic group" as used herein denotes an aromatic group having 4 to 18 carbon atoms.

"Alkyl" as used herein denotes straight chain or branched alkyl, which may be, e.g., $C_1$-$C_{10}$-alkyl, such as methyl, ethyl, n-propyl, isopropyl, n-butyl, isobutyl, sec-butyl, tert-butyl, straight- or branched-pentyl, straight- or branched-hexyl, straight- or branched-heptyl, straight- or branched-nonyl or straight- or branched-decyl. Preferably alkyl is $C_1$-$C_4$-alkyl.

"Aryl" as used herein denotes $C_6$-$C_{14}$-aryl, preferably $C_6$-$C_{10}$-aryl, and may be, e.g., substituted by at least one group selected from mercapto, dialkylamino, nitro, alkoxy, halogen, keto, cyano or a combination. Preferably aryl is phenyl.

"Alkoxy" as used herein denotes straight chain or branched alkoxy and may be, e.g., $C_1$-$C_{10}$-alkoxy, such as methoxy, ethoxy, n-propoxy, isopropoxy, n-butoxy, isobutoxy, sec-butoxy, tert-butoxy or straight- or branched-pentoxy, -hexyloxy, -heptyloxy, -octyloxy, -nonyloxy or -decyloxy. Preferably alkoxy is $C_1$-$C_4$-alkoxy.

"Alkenyl" as used herein denotes straight chain or branched-alkenyl, which may be, e.g., $C_2$-$C_{10}$-alkenyl, such as vinyl, 1-propenyl, 2-propenyl, 1-butenyl, isobutenyl, or straight- or branched-pentenyl, -hexenyl, -heptenyl, -octenyl, -nonenyl or -decenyl. Preferred alkenyl is $C_2$-$C_4$-alkenyl.

"Cycloalkyl" as used herein denotes $C_3$-$C_{10}$-cycloalkyl having 3- to 8-ring carbon atoms and may be, e.g., cyclopropyl, cyclobutyl, cyclopentyl, cyclohexyl, cycloheptyl or cycloheptyl, any of which can be substituted by one, two or more $C_1$-$C_4$alkyl groups, particularly methyl groups. Preferably, cycloalkyl is $C_3$-$C_6$-cycloalkyl.

"Benzocycloalkyl" as used herein denotes cycloalkyl, e.g., one of the $C_3$-$C_{10}$-cycloalkyl groups mentioned hereinbefore, attached at two adjacent carbon atoms to a benzene ring. Preferably, benzocycloalkyl is benzo-$C_5$-$C_6$cycloalkyl, especially, benzocyclohexyl (tetrahydronaphthyl).

"Cycloalkylalkyl" as used herein denotes $C_3$-$C_{10}$-cycloalkyl-$C_1$-$C_{10}$-alkyl, where the $C_3$-$C_{10}$-cycloalkyl group has 3- to 8-ring carbon atoms and may be, e.g., one of the $C_1$-$C_{10}$-alkyl groups mentioned hereinbefore, particularly one of the $C_1$-$C_4$-alkyl groups, substituted by one of the $C_3$-$C_{10}$-cycloalkyl groups mentioned hereinbefore. Preferably cycloalkylalkyl is $C_3$-$C_6$-Cycloalkyl-$C_1$-$C_4$-alkyl.

"Aralkyl" as used herein denotes straight-chain or branched-$C_6$-$C_{10}$-aryl-$C_1$-$C_{10}$-alkyl and may be, e.g., one of the $C_1$-$C_{10}$-alkyl groups mentioned hereinbefore, particularly one of the $C_1$-$C_4$-alkyl groups, substituted by phenyl, tolyl, xylyl or naphthyl. Preferably, aralkyl is phenyl-$C_1$-$C_4$-alkyl, particularly benzyl or 2-phenylethyl.

"Heterocyclic" as used herein denotes a monovalent heterocyclic group having up to 20 carbon atoms and one, two, three or four heteroatoms selected from nitrogen, oxygen and sulfur, the group optionally having an alkyl, alkylcarbonyl, hydroxyalkyl, alkoxyalkyl or aralkyl group attached to a ring carbon or nitrogen atom and being linked to the remainder of the molecule through a ring carbon atom, and may be, e.g., a group, preferably a monocyclic group, with one nitrogen, oxygen or sulfur atom, such as pyrryl, pyridyl, piperidyl, furyl, tetrahydrofuryl or thienyl, or a group, preferably a monocyclic group, with two hetero atoms selected from nitrogen, oxygen and sulfur, such as imidazolyl, pyrimidinyl, piperazinyl, oxazolyl, isoxazolyl, thiazolyl, morpholinyl or thiomorpholinyl. Preferably, heterocyclic is a monocyclic group having 5- or 6-ring atoms and one or two nitrogen atoms, or one nitrogen atom and one oxygen atom, in the ring and optionally substituted on a ring nitrogen atom by $C_1$-$C_4$-alkyl, hydroxy-$C_1$-$C_4$-alkyl, $C_1$-$C_4$-alkylcarbonyl or phenyl-$C_1$-$C_4$-alkyl.

"Heteroaralkyl" as used herein denotes straight-chain or branched heteroaralkyl, e.g. one of the $C_1$-$C_{10}$-alkyl groups mentioned hereinbefore, substituted by one or more heterocyclic groups.

"Haloalkyl" as used herein denotes straight-chain or branched-alkyl, e.g., $C_1$-$C_{10}$-alkyl, such as one of the $C_1$-$C_{10}$-alkyl groups mentioned hereinbefore, substituted by one or more, e.g., one, two or three, halogen atoms, preferably fluorine or chlorine atoms. Preferably haloalkyl is $C_1$-$C_4$alkyl substituted by one, two or three fluorine or chlorine atoms.

"Substituted silyl group" as used herein denotes is preferably a silyl group substituted with at least one alkyl group as herein defined.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

In a second aspect the present invention provides a process for preparing 5-[(R)-2-(5,6-diethyl-indan-2-ylamino)-1-hydroxy-ethyl]-8-hydroxy-(1H)-quinolinone-2-one salts comprising:

(a) reacting
  (i) 8-hydroxy-(1H)-quinolin-2-one with an acylating agent and a Lewis acid to form 5-acetyl-8-hydroxy-(1H)-quinolin-2-one; or
  (ii) 8-hydroxy-(1H)-quinolin-2-one with an acylating agent to form 8-acetoxy-(1H)-quinolin-2-one, and treating, in-situ, the 8-acetoxy-(1H)-quinolin-2-one with a Lewis acid to form 5-acetyl-8-hydroxy-(1H)-quinolin-2-one; or
  (iii) 8-acetoxy-(1H)-quinolin-2-one with a Lewis acid to form 5-acetyl-8-hydroxy-(1H)-quinolin-2-one;
(b) reacting the 5-acetyl-8-hydroxy-(1H)-quinolin-2-one prepared in Step (i) with a compound having the Formula RL in the presence of a base and a solvent to form 5-acetyl-8-substituted oxy-(1H)-quinolin-2-one, wherein R is a protecting group and L is a leaving group;
(c) reacting the 5-acetyl-8-substituted oxy-(1H)-quinolin-2-one with a halogenating agent in the presence of a solvent to form a 5-(α-haloacetyl)-8-substituted oxy-(1H)-quinolin-2-one;
(d) reacting an 5-(α-haloacetyl)-8-substituted oxy-(1H)-quinolin-2-one with a reducing agent in the presence of a chiral catalyst to form 8-(substituted oxy)-5-((R)-2-halo-1-hydroxy-ethyl)-(1H)-quinolin-2-one;
(e) treating the 8-(substituted oxy)-5-((R)-2-halo-1-hydroxy-ethyl)-(1H)-quinolin-2-one with a base in the presence of a solvent to form 8-(substituted oxy)-5-(R)-oxiranyl-(1H)-quinolin-2-one;
(f) reacting the 8-substituted oxy-5-(R)-oxiranyl-(1H)-quinolin-2-one having Formula (I)

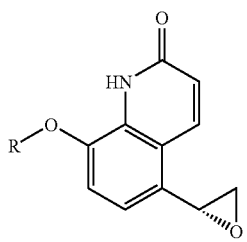

(I)

with 2-amino-(5-6-diethyl)-indan to form a reaction mixture containing compounds having Formulae (II), (II) and (IV)

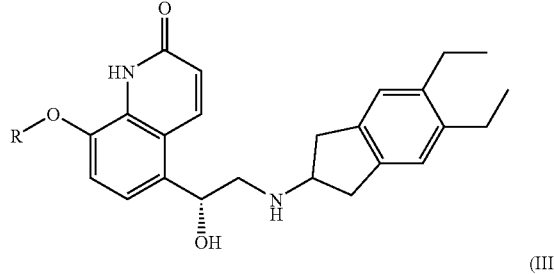

(II)

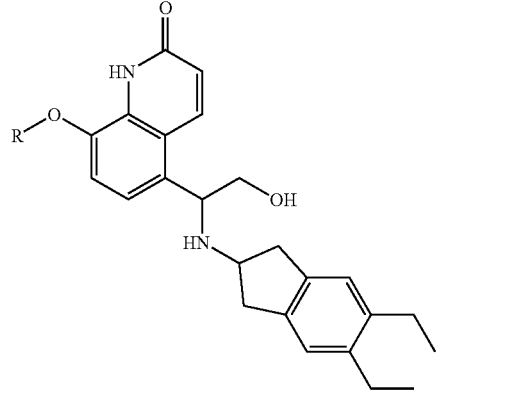

(III)

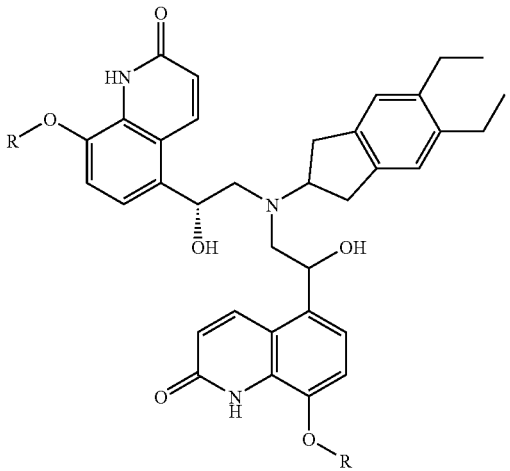

(IV)

wherein R is a protecting group;

(g) treating the reaction mixture prepared in Step (f) with an acid in the presence of a solvent to form a corresponding salt;

(h) isolating and crystallizing a salt having Formula (V)

(V)

wherein R is a protecting group and A− is an anion;

(i) removing the protecting group from the salt having Formula (V) in the presence of a solvent to form a salt having Formula (VI):

(VI)

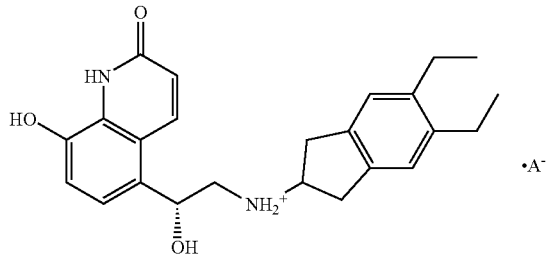

wherein A− is an anion; and (j) treating the salt having Formula (VI) with an acid in the presence of a solvent to form 5-[(R)-2-(5,6-diethyl-indan-2-ylamino)-1-hydroxy-ethyl]-8-hydroxy-(1H)-quinolin-2-one salt having Formula (VII)

(VII)

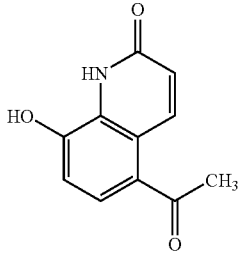

wherein X— is an anion.

The 8-hydroxy-(1H)-quinolin-2-one has Formula (VIII)

(VIII)

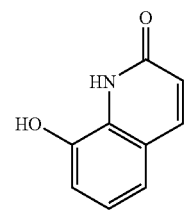

The 5-acetyl-8-hydroxy-(1H)-quinolin-2-one has Formula (IX)

(IX)

Preferably, the acylating agent is acetic anhydride or acetyl chloride.

Preferably, the acylating agent is present in an amount of from about 1 molar equivalents to about 1.5 molar equivalents, more preferably about 1.05 molar equivalents, based on the molar equivalents of 8-hydroxy-(1H)-quinolin-2-one.

The Lewis acid is preferably selected from boron trifluoride ($BF_3$), aluminium chloride ($AlCl_3$), and titanium tetrachloride ($TiCl_4$). More preferably, the Lewis acid is aluminium chloride. A combination of Lewis acids may also be used.

The Lewis acid is present in an amount of greater than 2 molar equivalents, based on the molar equivalents of 8-hydroxy-(1H)-quinolin-2-one or molar equivalents of 8-acetoxy-(1H)-quinolin-2-one. Preferably, the Lewis acid is present in an amount of about 3 molar equivalents to about 5 molar equivalents, more preferably from about 3.2 molar equivalents to about 4 molar equivalents.

In one embodiment of the invention, Step (a) is conducted in the presence of a solvent. In another embodiment of the invention, Step (a) is conducted in the absence of a solvent and in the presence of an ionic compound. The ionic compound is an ionic liquid or an alkaline halide.

Preferably a solvent is used in Step (a). The solvent is preferably a solvent compatible with Friedel-Craft conditions. Such solvents are well-known to those skilled in the art and include methylenechloride, 1,2-ethylene dichloride, chlorobenzene, o-dichlorobenzene, aliphatic $C_6$-$C_{12}$ hydrocarbons, e.g., isooctane, heptane and combinations thereof. A combination of solvents may also be used. A preferred solvent for use in Step (a) is o-dichlorobenzene.

Step (a) may be conducted in the absence of a solvent and in the presence of an ionic compound selected from an alkaline halide and an ionic liquid. The alkaline halide is preferably selected from sodium chloride, sodium bromide, lithium chloride and lithium bromide. More preferably, the alkaline halide is sodium chloride. A combination of alkaline halides may also be used.

Ionic liquids are characterized by a positively-charged cation and a negatively-charged anion. Generally, any molten salt or mixture of molten salts is considered an ionic liquid. Ionic liquids typically have essentially no vapour pressure, good heat transfer characteristics, are stable over a wide temperature range and are capable of dissolving a wide range of material in high concentrations. As used herein, "essentially no vapour pressure" means that the ionic liquid exhibits a vapour pressure of less than about 1 mm/Hg at 25° C., preferably less than about 0.1 mm/Hg at 25° C.

With respect to the type of ionic liquid, a wide variety of possibilities exist. However, the preferred ionic liquids are liquid at relatively low temperatures. Preferably, the ionic liquid has a melting point of less than 250° C., more preferably less than 100° C. Most preferably, the ionic liquid has a melting point of less than 30° C. and is a liquid at room temperature. Preferably, the ionic liquid has a viscosity of less than 500 centipoise (cP), more preferably, less than 300 cP, and most preferably less than 100 cP, as determined at 25° C.

The cation present in the ionic liquid can be a single species or a plurality of different species. Both of these embodiments are intended to be embraced, unless otherwise specified, by the use of the singular expression "cation". The cations of the ionic liquid include organic and inorganic cations. Examples of cations include quaternary nitrogen-containing cations, phosphonium cations and sulfonium cations.

The quaternary nitrogen-containing cations are not particularly limited and embrace cyclic, aliphatic and aromatic quaternary nitrogen-containing cations. Preferably, the quaternary nitrogen-containing cation is an n-alkyl pyridinium, a dialkyl imidazolium or an alkyl-ammonium of the formula $R'_{4-x}PH_x$, wherein x is 0-3 and each R' is independently an alkyl group having 1-18 carbon atoms. It is believed that unsymmetrical cations can provide for lower melting temperatures. The phosphonium cations are not particularly limited and embrace cyclic, aliphatic and aromatic phosphonium cations. Preferably, the phosphonium cations include those of the formula $R''_{4-x}PH_x$, wherein x is 0-3, and each R" is an alkyl or aryl group, such as an alkyl group having 1-18 carbon atoms or a phenyl group. The sulfonium cations are not particularly limited and embrace cyclic, aliphatic and aromatic sulfonium cations. Preferably, the sulfonium cations include those of the formula $R'''_{3-x}SH_x$, wherein x is 0-2 and each R''' is an alkyl or aryl group, such as an alkyl group having 1-18 carbon atoms or a phenyl group. Preferred cations include 1-hexylpyridinium, ammonium, imidazolium, 1-ethyl-3-methylimidazolium, 1-butyl-3-methylimidazolium, phosphonium and N-butylpyridinium.

The anion used in the ionic liquid is not particularly limited and includes organic and inorganic anions. Generally the anion is derived from an acid, especially a Lewis acid. The anions are typically metal halides as described in more detail below, boron or phosphorus fluorides, alkylsulfonates including fluorinated alkyl sulfonates, such as nonafluorobutanesulfonate; and carboxylic acid anions, such as trifluoroacetate and heptafluorobutanoate.

The anion is preferably Cl—, Br—, $NO_2$—, $NO_3$—, $AlCl_4$—, $BF_4$—, $PF_6$—, $CF_3COO$—, $CF_3SO_3$—, $(CF_3SO_2)_2N$—, OAc—, $CuCl_3$—, $GaBr_4$—, $GaCl_4$— and $SbF_6$—.

Examples of ionic liquids include, but are not limited to, imidazolium salts, pyridium salts, ammonium salts, phosphonium salts and sulphonium salts. Preferred imidazolium salts have Formula (X)

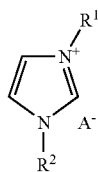

wherein
$R^1$ and $R^2$ are, independently, selected from the group consisting of a $C_1$-$C_{18}$-aliphatic group and a $C_4$-$C_{18}$-aromatic group; and
A– is an anion.

Preferred ammonium salts have Formula (XI)

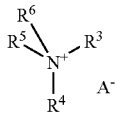

wherein
$R^3$, $R^4$, $R^5$ and $R^6$ are, independently, selected from the group consisting of a $C_1$-$C_{18}$-aliphatic group and a $C_4$-$C_{18}$-aromatic group; and
A– is an anion.

Preferably, $R^3$, $R^4$, $R^5$ and $R^6$ are, independently, selected from the group consisting of ethyl, propyl and butyl.

Preferred phosphonium salts have Formula (XII)

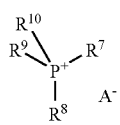

wherein
$R^7$, $R^8$, $R^9$ and $R^{10}$ are, independently, selected from the group consisting of a $C_1$-$C_{18}$-aliphatic group and a $C_4$-$C_{18}$-aromatic group; and
A– is an anion.

Preferably, $R^7$, $R^8$, $R^9$ and $R^{10}$ are, independently, selected from the group consisting of ethyl and butyl.

Preferred pyridinium salts have Formula (XIII)

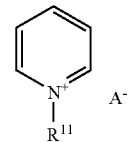

wherein
$R^{11}$ is selected from the group consisting of a $C_1$-$C_{18}$-aliphatic group and a $C_4$-$C_{18}$ aromatic group; and
A– is an anion.

Preferably $R^{11}$ is ethyl or butyl.

Specific examples of ionic liquids include, but are not limited to, 1-butyl-3-methylimidazolium hexafluorophosphate, 1-hexyl-3-methylimidazolium hexafluorophosphate, 1-octy-3-methylimidazolium hexafluorophosphate, 1-decyl-3-methylimidazolium hexafluoro-phosphate, 1-dodecyl-3-methylimidazolium hexafluorophosphate, 1-ethyl-3-methylimidazolium bis((trifluoromethyl)sulphonyl)-imidate, 1-hexyl-3-methylimidazolium bis((trifluoro-methyl)sulphonyl)amide, 1-hexylpyridinium tetrafluoroborate, 1-octylpyridinium tetra-fluoroborate, 1-butyl-3-methylimidazolium tetrafluoroborate, 1-methy-3-ethyl imidazolium chloride, 1-ethyl-3-butyl imidazolium chloride, 1-methy-3-butyl imidazolium chloride, 1-methy-3-butyl imidazolium bromide, 1-methy-3-propyl imidazolium chloride, 1-methy-3-hexyl imidazolium chloride, 1-methy-3-octyl imidazolium chloride, 1-methy-3-decyl imidazolium chloride, 1-methy-3-dodecyl imidazolium chloride, 1-methy-3-hexadecyl imidazolium chloride, 1-methy-3-octadecyl imidazolium chloride, 1-methy-3-octadecyl imidazolium chloride, ethyl pyridinium bromide, ethyl pyridinium chloride, ethylene pyridinium dibromide, ethylene pyridinium dichloride, butyl pyridinium chloride and benzyl pyridinium bromide.

Preferred ionic liquids are 1-ethyl-3-methyl-imidazolium trifluoroacetate, 1-butyl-3-methyl-imidazolium trifluoroacetate, 1-ethyl-3-methyl-imidazolium trifluoroacetate, 1-butyl-3-methyl-imidazolium hexafluorophosphate, 1-octyl-3-methyl-imidazolium hexafluoro-phosphate, 1-hexyl-3-methy-imidazolium hexafluorophosphate, 1-butyl-3-methyl-imidazolium hexafluorophosphate, 1-butyl-3-methyl-imidazolium tetrafluoroborate, 1-ethyl-3-methyl-imidazolium tetrafluoroborate, 1-octyl-3-methyl-imidazolium bromide, 1-ethyl-3-methyl-imadazolium trifluorosulfonate, 1-butyl-3-methyl-imidazolium trifluorosulfonate, 1-butyl-3-methyl-imidazolium trifluoromethanesulfonate, 1-ethyl-3-methyl-imidazolium trifluoromethanesulfonate and 1-ethyl-3-methyl-imidazolium bis-(trifluoromethanesulfonyl)-imidate. Most preferably, the ionic liquid is selected from 1-ethyl-3-methyl-imidazolium trifluorosulfonate, 1-butyl-3-methylimidazolium chloride, 1-octyl-3-methyl-imidazolium hexafluorophosphate and 1-hexyl-3-methyl-imidazolium hexafluorophosphate. A combination of ionic liquids may also be used.

Mixtures of ionic compounds and Lewis acids may form reactive liquids at low temperature (see Wasserscheid et al., Angew. Chem. Int. Ed., Vol. 39, pp. 3772-3789 (2000)).

Preferably, the weight ratio of Lewis acid to ionic compound is from about 10 to about 0.1, respectively. More preferably, the ratio of Lewis acid to ionic compound is from about 3 to about 1, respectively.

The temperature used in Step (a) is preferably from about 0° C. to about 160° C. More preferably, the temperature is from about 10° C. to about 120° C.; and most preferably from about 15° C. to about 100° C.

The 5-acetyl-8-hydroxy-(1H)-quinolin-2-one product prepared in Step (a) may also be present with 7-acetyl-8-hydroxy-(1H)-quinolin-2-one having Formula (XIV)

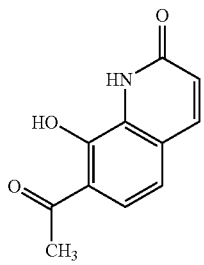

(XIV)

The 5-acetyl-8-hydroxy-(1H)-quinolin-2-one may be recovered from the reaction mixture and purified by any of the various techniques known to the art, such as by crystallization or forming a slurry in a solvent. A preferred solvent for forming a slurry is acetic acid.

In the second step, Step (b), the 5-acetyl-8-hydroxy-(1H)-quinolin-2-one that is prepared in Step (a) is reacted with a compound having the Formula RL in the presence of a base and a solvent to form 5-acetyl-8-substituted oxy-(1H)-quinolin-2-one, wherein R is a protecting group and L is a leaving group.

The 5-acetyl-8-substituted oxy-(1H)-quinolin-2-one has Formula (XV)

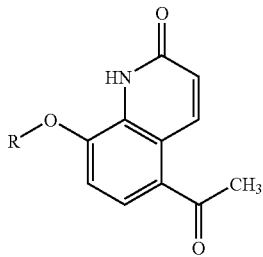

(XV)

wherein R is a protecting group.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Third Edition, 1999, which reference also describes procedures suitable for replacement of the protecting groups by hydrogen.

Preferred protecting groups are phenol protecting groups which are known to those skilled in the art. More preferably, the protecting group is selected from alkyl, alkenyl, aryl, (cycloalkyl)alkyl, arylalkyl, cycloalkyl and a substituted silyl group. The alkyl or aryl group has from 1-24 carbon atoms, more preferably 6-12 carbon atoms. The substituted silyl group is preferably substituted with at least one alkyl group. Most preferably, the protecting group is benzyl or t-butyldimethylsilyl.

Preferably, the compound having the formula RL is an alkyl halide or substituted alkyl halide, such as α-methylbenzyl bromide, methyl chloride, benzylchloride and benzylbromide. Preferred bases include sodium ethoxide, sodium hydroxide, potassium hydroxide, potassium phosphate, potassium carbonate, potassium hydrogencarbonate, caesium carbonate, pyridine and trialkylamines such as triethylamine, tributylamine and N,N-diisopropylethylamine. A combination of bases may also be used. Preferred bases are potassium hydroxide, potassium carbonate and potassium hydrogencarbonate. Most preferably, the base is N,N-diisopropylethylamine.

The solvent in Step (b) is preferably selected from an alkyl acetate, e.g., $C_1$-$C_6$-alkyl acetates, such as ethyl acetate, isopropyl acetate and butyl acetate; lower alkyl alcohols, e.g., $C_1$-$C_6$-alkyl alcohols, such as methanol, ethanol, propanol, butanol and pentanol; dimethyl-formamide; dialkyl ketones, e.g., acetone and methyl isobutyl ketone; acetonitrile; heterocycles, such as tetrahydrofuran; dialkyl ethers, e.g., diisopropyl ether, 2-methoxyethyl ether and diethylene ether; aqueous solvents, such as water; ionic liquids; and chlorinated solvents, such as methylenechloride. A combination of solvents may also be used. A preferred solvent for use in Step (b) is an acetone/water mixture. A preferred volume ratio of acetone to water is from 10:90 to 90:10, respectively. More preferably, the volume ratio of acetone to water is from 20:80 to 80:20, respectively. Most preferably, the volume ratio of acetone to water is about 75:25.

The temperature used in Step (b) is preferably from about 20° C. to about 90° C. More preferably, the temperature is from about 30° C. to about 80° C.; and most preferably from about 50° C. to about 70° C.

The 5-acetyl-8-substituted oxy-(1H)-quinolin-2-one is preferably 5-acetyl-8-benzyloxy-(1H)-quinolin-2-one.

Optionally, the 5-acetyl-8-substituted oxy-(1H)-quinolin-2-one product may be purified by any of the various techniques known to the art, such as by crystallization.

In the third step, Step (c), the 5-acetyl-8-substituted oxy-(1H)-quinolin-2-one that is prepared in Step (b) is reacted with a halogenating agent in the presence of a solvent to form 5-(α-haloacetyl)-8-substituted oxy-(1H)-quinolin-2-one.

The 5-(α-haloacetyl)-8-substituted oxy-(1H)-quinolin-2-one has Formula (XVI)

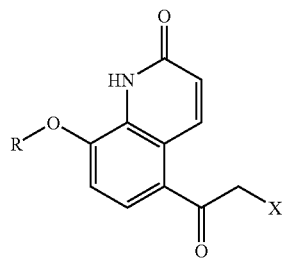

(XVI)

wherein
R is a protecting group; and
X is a halogen.

The halogenating agent may be any compound or combination of compounds that provide a halogen atom in situ. Preferred halogenating agents include sodium bromate and hydrobromic acid, bromine, N-bromosuccinimide, N-chlorosuccinimide, iodine, chlorine, sulfuryl chloride, benzyltrimethylammoniumdichloroiodate, copper chloride, pyridinium tribromide, tetraalkylammonium tribromide, iodine chloride, hydrochloric acid and an oxidating agent, such as oxone, hydrogen peroxide and monoperoxyphthalic acid. A combination of halogenating agents may also be used. Most preferably, the halogenating agent is benzyltrimethylammoniumdichloroiodate. It is within the scope of the invention to use sulfuryl chloride with methanol.

The solvent used in Step (c) is preferably selected from an acid, e.g., carboxylic acids, such as acetic acid, trifluoroacetic acid and propionic acid; an alkyl acetate, e.g., $C_1$-$C_6$-alkyl acetates, such as ethyl acetate, isopropyl acetate and butyl acetate; dimethylformamide; aromatic hydrocarbons, such as toluene and benzene; acetonitrile; heterocycles, such as tetrahydrofuran; dialkyl ethers, e.g., diisopropyl ether, 2-methoxyethyl ether and diethylene ether; ionic liquids; and chlorinated solvents, such as methylenechloride. A combination of solvents may also be used. A preferred solvent for use in Step (c) is acetic acid.

The temperature used in Step (c) is preferably from about 10° C. to about 160° C. More preferably, the temperature is from about 20° C. to about 120° C.; and most preferably from about 60° C. to about 75° C.

The 5-(α-haloacetyl)-8-substituted oxy-(1H)-quinolin-2-one product is preferably 5-(α-chloroacetyl)-8-benzyloxy-(1H)-quinolin-2-one.

Optionally, the 5-(α-haloaceryl)-8-substituted oxy-(1H)-quinolin-2-one product may be purified by any of the various techniques known to the art, such as by crystallization.

As mentioned above, 5-α-haloacetyl)-8-benzyloxy-(1H)-quinolin-2-ones, for example 5-α-chloroacetyl)-8-benzyloxy-(1H)-quinolin-2-one, are useful intermediates from which to prepare 5-[(R)-2-(5,6-diethyl-indan-2-ylamino)-1-hydroxy-ethyl]-8-hydroxy-(1H)-quinolinone-2-one salts. In fact 5-(α-haloacetyl)-8-benzyloxy-(1H)-quinolin-2-ones are useful intermediates from which to prepare 8-substituted oxy-5-(R)-oxiranyl-(1H)-quinolin-2-ones, which in turn are useful intermediates from which to prepare 5-[(R)-2-(5,6-diethyl-indan-2-ylamino)-1-hydroxy-ethyl]-8-hydroxy-(1H)-quinolinone-2-one salts.

The 8-substituted oxy-5-(R)-oxiranyl-(1H)-quinolin-2-one may be prepared by reacting an 8-(substituted oxy)-5-haloacetyl-(1H)-quinolin-2-one formed in step (c) with a reducing agent in the presence of a chiral catalyst according to step (d) to form 8-(substituted oxy)-5-((R)-2-halo-1-hydroxy-ethyl)-(1H)-quinolin-2-one; and then treating the 8-(substituted oxy)-5-((R)-2-halo-1-hydroxy-ethyl)-(1H)-quinolin-2-one formed in step (d) with a base in the presence of a solvent according to step (e) to form 8-(substituted oxy)-5-(R)-oxiranyl-(1H)-quinolin-2-one.

For example, in Step (d), the 8-substituted oxy-5-haloacetyl-(1H)-quinolin-2-one is reacted with a reducing agent in the presence of a chiral catalyst to form a 8-substituted oxy-5-((R)-2-halo-1-hydroxy-ethyl)-(1H)-quinolin-2-one of Formula (XVII):

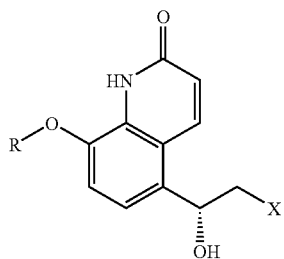

(XVII)

wherein R is a protecting group; and X is a halogen. The halogen is selected from bromine, chlorine, fluorine and iodine. Preferably, the halogen is chlorine.

Preferably, the chiral catalyst is an oxazaborolidine compound of Formula (XVIII):

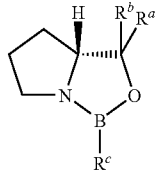

(XVIII)

wherein $R^a$ and $R^b$ are, independently, selected from an aliphatic, cycloaliphatic, cycloaliphatic-aliphatic, aryl or aryl-aliphatic residue. Preferably, $R^a$ and $R^b$ are, independently, selected from phenyl, 4-methylphenyl, and 3,5-dimethylphenyl. More preferably, $R^a$ and $R^b$ are phenyl, and $R^c$ is selected from aliphatic, cycloaliphatic, cycloaliphatic-aliphatic, aryl or aryl-aliphatic residue, which, in each case, may be linked to a polymer. More preferably, $R^c$ is methyl.

$R^a$, $R^b$ and $R^c$ are preferably unsubstituted but may be substituted, example, by one or more, e.g., two or three, residues, e.g., those selected from $C_1$-$C_7$-alkyl, hydroxy, —O—$CH_2$—O—, —CHO, $C_1$-$C_7$-substituted oxy, $C_2$-$C_8$-alkanoyl-oxy, halogen, e.g., chlorine or fluorine, nitro, cyano and $CF_3$.

Aliphatic hydrocarbon residues include $C_1$-$C_7$-alkyl, $C_2$-$C_7$-alkenyl or secondarily $C_2$-$C_7$-alkynyl. $C_2$-$C_7$-Alkenyl is, in particular, $C_3$-$C_7$-alkenyl and is, e.g., 2-propenyl or 1-, 2- or 3-butenyl. $C_3$-$C_5$-Alkenyl is preferred. $C_2$-$C_7$-Alkynyl is, in particular, $C_3$-$C_7$-alkynyl and is preferably propylnyl.

Cycloaliphatic residues include $C_3$-$C_8$-cycloalkyl or, secondarily, $C_3$-$C_8$-cycloalkenyl. $C_3$-$C_8$-cycloalkyl is preferably cyclopentyl or cyclohexyl. $C_3$-$C_8$-cycloalkenyl is $C_3$-$C_7$-cycloalkenyl is preferably cyclopent-2-en-yl and cyclopent-3-enyl, or cyclohex-2-en-yl and cyclohex-3-en-yl.

Cycloaliphatic-aliphatic residues include $C_3$-$C_8$-cycloalkyl-$C_1$-$C_7$-alkyl, preferably $C_3$-$C_6$-cycloalkyl-$C_1$-$C_4$-alkyl, but especially cyclopropylmethyl.

The aryl residue may be, for example, a carbocyclic or heterocyclic aromatic residue, in particular, phenyl or, in particular, an appropriate 5- or 6-membered and mono or multicyclic residue which has up to four identical or different hetero atoms, such as nitrogen, oxygen or sulfur atoms, preferably one, two, three or four nitrogen atoms, an oxygen atom or a sulfur atom. Suitable 5-membered heteroaryl residues include monoaza-, diaza-, triaza-, tetraaza-, monooxa- or monothia-cyclic aryl radicals, such as pyrrolyl, pyrazolyl, imidazolyl, triazolyl, tetrazolyl, furyl and thienyl, while suitable appropriate 6-membered residues are, in particular, pyridyl. Appropriate multicyclic residues are anthracenyl, phenanthryl, benzo-[1,3]-dioxole or pyrenyl. An aryl residue may be mono-substituted by, e.g., $NH_2$, OH, $SO_3H$, CHO or di-substituted by OH or CHO and $SO_3H$.

Aryl-aliphatic residues include phenyl-$C_1$-$C_7$ alkyl, phenyl-$C_2$-$C_7$ alkenyl and phenyl-$C_2$-$C_7$ alkynyl.

Suitable polymers include polystyrene (PS), cross-linked PS (J), polyethylene glycol (PEG) or a silica gel residue (Si). Examples are NH—$R^d$, wherein $R^d$ is $C(O)(CH_2)_n$—PS or $C(O)NH(CH_2)_n$—PS; and —O—$Si(R^e)_2(CH_2)_nR^f$, wherein n is 1-7, $R^e$ is $C_1$-$C_6$ alkyl, e.g., ethyl, and $R^f$ is a polystyrene, cross-linked polystryrene, polyethylene glycol or a silica gel residue.

The reducing agent that is used to reduce the 8-(substituted oxy)-5-haloacetyl-(1H)-quinolin-2-one is preferably a borane reagent such as borane-tetrahydrofuran complex, a borane-N,N-diethylaniline complex or a borane-methyl sulfide complex. A borane-tetrahydrofuran complex is especially preferred. The oxazaborolidine chiral catalyst is preferably (R)-tetrahydro-1-methyl-3,3-diphenyl-(1H,3H)-pyrrolo[1,2-c][1,3,2]-oxazaborole, also known as (R)-2-methyl-CBS-oxazaborolidine (Me-CBS).

Preferably a solvent is used in Step (d). Preferred solvents include: an alkyl acetate, e.g., $C_1$-$C_6$-alkyl acetates, such as ethyl acetate, isopropyl acetate and butyl acetate; alkylamines, e.g., $C_1$-$C_6$ alkylamines; lower alkyl alcohols, e.g., $C_1$-$C_6$-alkyl alcohols, such as methanol, ethanol, propanol, isopropanol, butanol, and pentanol; aliphatic $C_6$-$C_{12}$-hydrocarbons, e.g., isooctane, heptane; dimethylformamide; aromatic hydrocarbons, such as toluene and benzene; acetonitrile; heterocycles, such as tetrahydrofuran; dialkyl ethers, e.g., diisopropyl ether, 2-methoxyethyl ether, and diethylene ether; aqueous solvents, such as water; ionic liquids; and chlorinated solvents, such as methylenechloride. A combination of solvents may also be used. The preferred solvent for use in Step (d) is tetrahydrofuran.

The temperature used in Step (d) is preferably from about −10° C. to about 80° C. More preferably, the temperature is from about 0° C. to about 50° C.

The 8-substituted oxy-5-((R)-2-halo-1-hydroxy-ethyl)-(1H)-quinolin-2-one is preferably 8-phenylmethoxy-5-((R)-2-chloro-1-hydroxy-ethyl)-(1H)-quinolin-2-one. Optionally, the 8-substituted oxy-5-((R)-2-halo-1-hydroxy-ethyl)-(1H)-quinolin-2-one product may be purified by any of the various techniques known to the art, such as by crystallization, and may, optionally, be conducted in the presence of charcoal.

In Step (e) the 8-substituted oxy-5-((R)-2-halo-1-hydroxy-ethyl)-(1H)-quinolin-2-one is treated with a base in the presence of a solvent to form 8-substituted oxy-5-(R)-oxiranyl-(1H)-quinolin-2-one. The 8-substituted oxy-5-(R)-oxiranyl-(1H-quinolin-2-one has Formula (XIX):

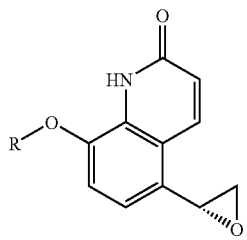

(XIX)

wherein R is a protecting group.

Preferred bases include sodium ethoxide, sodium hydroxide, potassium phosphate, potassium carbonate, potassium hydrogencarbonate and caesium carbonate. A combination of bases may also be used. The base is most preferably potassium-carbonate.

The solvent used in Step (e) is preferably selected from an alkyl acetate, e.g., $C_1$-$C_6$-alkyl acetates, such as ethyl acetate, isopropyl acetate and butyl acetate; alcohols, e.g., $C_1$-$C_6$-alkyl alcohols, such as methanol, ethanol, propanol, butanol, and pentanol; aliphatic $C_6$-$C_{12}$-hydrocarbons, e.g., isooctane, heptane; dimethylformamide; aromatic hydrocarbons, such as toluene and benzene; dialkyl ketones, e.g., acetone, methyl isobutyl ketone; acetonitrile; heterocycles, such as tetrahydrofuran; dialkyl ethers, e.g., diisopropyl ether, 2-methoxyethyl ether, and diethylene ether; aqueous solvents, such as water; ionic liquids; and chlorinated solvents such as methylenechloride. A combination of solvents may also be used. A preferred solvent for use in Step (e) is a combination of acetone and water.

The temperature used in Step (e) is preferably from about 10° C. to about 160° C. More preferably, the temperature is from about 30° C. to about 80° C.; and most preferably from about 50° C. to about 60° C.

The 8-substituted oxy-5-(R)-oxiranyl-(1H)-quinolin-2-one is preferably 8-phenylmethoxy-5-(R)-oxiranyl-(1H)-quinolin-2-one.

Optionally, the 8-substituted oxy-5-(R)-oxiranyl-(1H)-quinolin-2-one product is purified by any of the various techniques known to the art, such as by crystallization.

Crystallization from toluene or acetone is especially preferred, and may, optionally, be conducted in the presence of charcoal.

8-Substituted oxy-5-(R)-oxiranyl-(1H)-quinolin-2-ones are useful intermediates from which to prepare 5-[(R)-2-(5,6-diethyl-indan-2-ylamino)-1-hydroxy-ethyl]-8-hydroxy-(1H)-quinolinone-2-one salts. This is achieved by carrying out Steps (f) through (I).

In Step (f) 8-substituted oxy-5-(R)-oxiranyl-(1H)-quinolin-2-one having Formula (I)

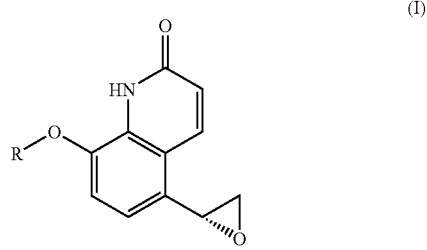

(I)

is reacted with 2-amino-(5-6-diethyl)-indan to form a reaction mixture containing compounds having Formulae (II), (III), (IV):

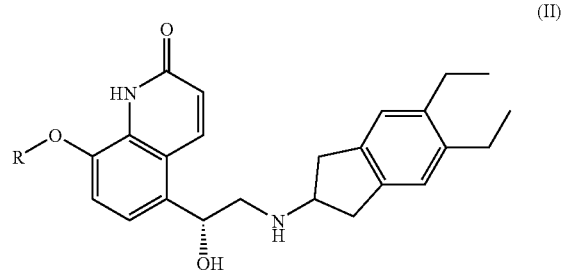

(II)

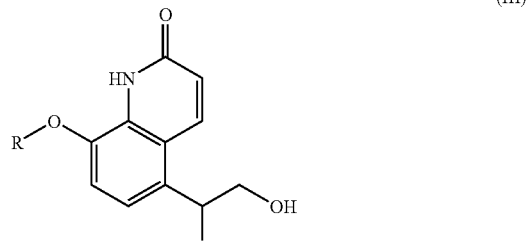

(III)

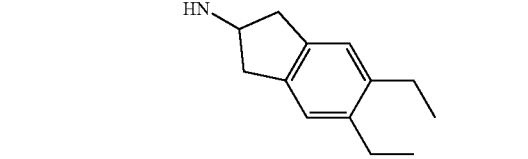

-continued

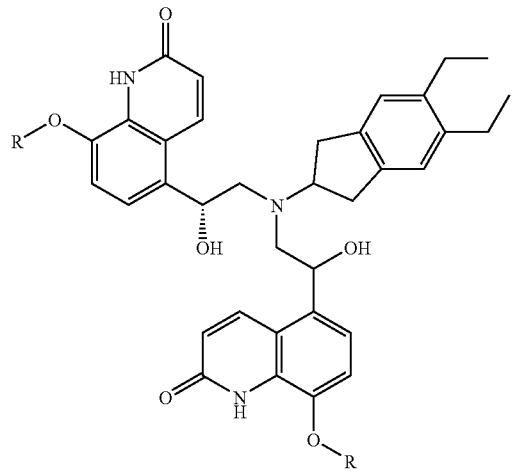

(IV)

wherein R is a protecting group.

Preferred protecting groups are phenol protecting groups which are known to those skilled in the art. More preferably, the protecting group is selected from the group consisting of an alkyl, aryl, alkoxy, alkenyl, cycloalkyl, benzocycloalkyl, cycloalkylalkyl, aralkyl, heterocyclic, heteroaralkyl, haloalkyl, and a substituted silyl group. Most preferably, the protecting group is benzyl or t-butyldimethylsilyl.

Preferably, Step (f) is conducted in the presence of a solvent. Preferred solvents include: alcohols, e.g., $C_{1-6}$-alkyl alcohols, such as methanol, ethanol, propanol, butanol, and pentanol; aliphatic $C_{6-12}$ hydrocarbons, e.g., isooctane, heptane;dimethylformamide; aromatic hydrocarbons, such as toluene and benzene; acetonitrile; heterocycles, such as tetrahydrofuran; dialkyl ethers, e.g., diisopropyl ether, 2-methoxyethyl ether and diethylene ether; dimethyl sulfoxide; tetrahydrothiophene 1,1-dioxide, also known as tetramethylene sulfone or as tetramethylene sulfolane; dialkyl carbonate, e.g., dimethyl carbonate and diethyl carbonate; aqueous solvents, such as water; ionic liquids; and chlorinated solvents, such as methylenechloride. A combination of solvents may also be used. More preferably, the solvent is 2-methoxyethyl ether or butanol.

The temperature used in Step (f) is preferably from about 10° C. to about 160° C. More preferably, the temperature is from about 30° C. to about 120° C.; and most preferably from about 90° C. to about 120° C.

Preferably, Step (f) is conducted with a molar excess of the 2-amino-(5-6-diethyl)-indan with respect to the 8-substituted oxy-5-(R)-oxiranyl-(1H)-quinolin-2-one. Preferably, 1.05 mole equivalent to 3 mole equivalents of 2-amino-(5-6-diethyl)-indan is used with respect to 8-substituted oxy-5-(R)-oxiranyl-(1H)-quinolin-2-one. Most preferably, 1.1 mole equivalents to 1.5 mole equivalents of 2-amino-(5-6-diethyl)-indan is used with respect to 8-substituted oxy-5-(R)-oxiranyl-(1H)-quinolin-2-one.

The 8-substituted oxy-5-(R)-oxiranyl-(1H)-quinolin-2-one is preferably 8-phenylmethoxy-5-(R)-oxiranyl-(1H)-quinolin-2-one. The 5-[(R)-2-(5,6-diethyl-indan-2-ylamino)-1-hydroxy-ethyl]-8-substituted oxy-(1H)-quinolin-2-one is preferably 5-[(R)-2-(5,6-diethyl-indan-2-ylamino)-1-hydroxy-ethyl]-8-phenylmethoxy-(1H)-quinolin-2-one.

In Step (g) the reaction mixture prepared in Step (f) is treated with an acid in the presence of a solvent to form a corresponding salt.

Preferred solvents for use in Step (g) include: alcohols, e.g. $C_1$-$C_6$-alkyl alcohols, such as methanol, ethanol, propanol, butanol, and pentanol; aliphatic $C_6$-$C_{12}$-hydrocarbons, e.g., isooctane, heptane;dimethylforinamide; aromatic hydrocarbons, such as toluene and benzene; acetonitrile; heterocycles, such as tetrahydrofuran; dialkyl ethers, e.g., diisopropyl ether, 2-methoxyethyl ether and diethylene ether; dimethyl sulfoxide; tetrahydrothiophene 1,1-dioxide, also known as tetramethylene sulfone or as tetramethylene sulfolane; dialkyl carbonate, e.g., dimethyl carbonate and diethyl carbonate; aqueous solvents, such as water; ionic liquids; and chlorinated solvents, such as methylenechloride. A combination of solvents may also be used. More preferably, the solvent is ethanol.

The temperature used in Step (g) is preferably from about −10° C. to about 160° C. More preferably, the temperature is from about 0° C. to about 120° C.; and most preferably from about 0° C. to about 75° C.

In Step (h) a salt having Formula (V)

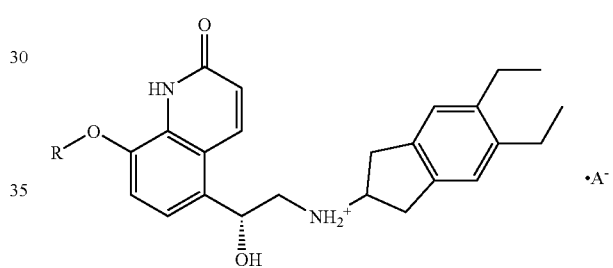

(V)

is isolated and crystallized, wherein R is a protecting group; and A− is an anion. The anion corresponds to the acid used in Step (g). The acid used in Step (g) is preferably a carboxylic acid, such as benzoic acid, maleic acid, succinic acid, fumaric acid, or tartaric acid; or a mineral acid, such as hydrochloric acid. Most preferably, the acid used in Step (g) is benzoic acid.

The salt having Formula (V) is preferably a benzoate salt having Pormula (XX)

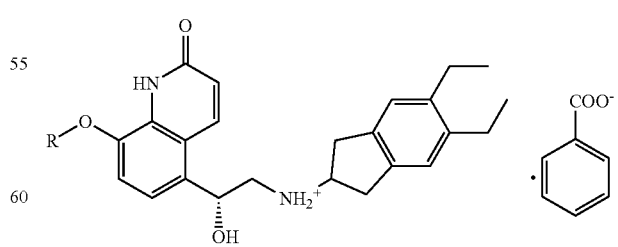

(XX)

wherein R is a protecting group.

More preferably, the benzoate salt having Formula (XX) is a benzoate salt having Formula (XXI)

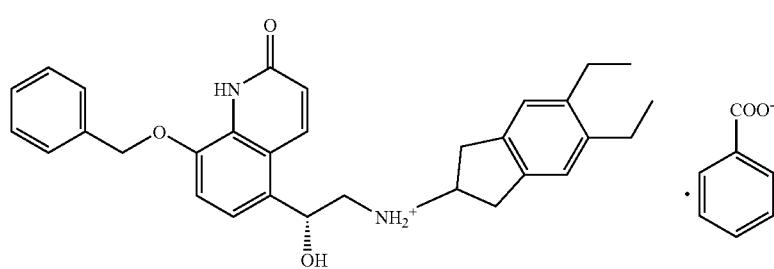

(XXI)

In Step (i) the protecting group on the salt having Formula (V) is removed in the presence of a solvent to form a salt having Formula (VI)

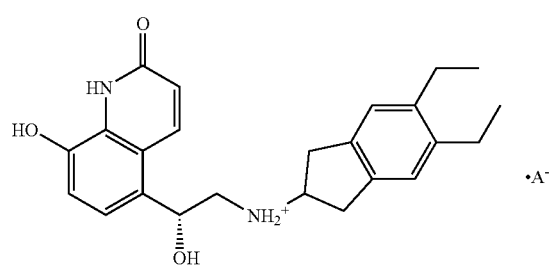

(VI)

wherein A– is an anion.

The salt having Formula (VI) is preferably a benzoate salt having Formula (XXII)

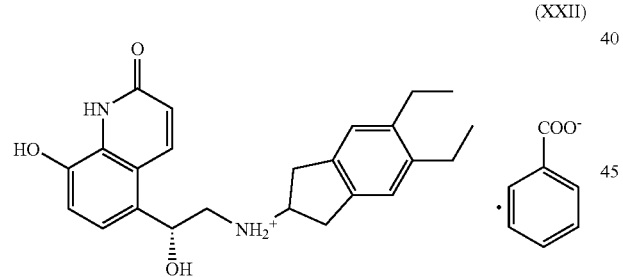

(XXII)

The removal of a protecting group is known to those skilled in the art and depends on the type of protecting group. In one embodiment where the protecting group is benzyl, a preferred method of removing the benzyl group on the salt having Formula (V) is by treating the salt with hydrogen in the presence of a catalyst. Preferred catalysts include palladium, palladium hydroxide, palladium on activated carbon, palladium on alumina, palladium on carbon powder, platinum, platinum on activated carbon and Raney™ nickel. A combination of catalysts may also be used. Most preferably, the catalyst is palladium on activated carbon.

In one embodiment where the protecting group is t-butyldimethylsilyl, a preferred method of removing the t-butyldimethylsilyl group on the salt having Formula (V) is by treating the salt with t-butylammonium fluoride or potassium fluoride.

The solvent used in Step (i) is preferably selected from an alkyl acetate, e.g., $C_1$-$C_6$-alkyl acetates, such as ethyl acetate, isopropyl acetate and butyl acetate; lower alkyl alkylamines, e.g., $C_1$-$C_6$-alkylamines; alcohols, e.g., $C_1$-$C_6$-alkyl alcohols, such as methanol, ethanol, propanol, butanol and pentanol; aliphatic $C_6$-$C_{12}$-hydrocarbons, e.g., isooctane, heptane, dimethylformamide; aromatic hydrocarbons, such as toluene and benzene; acetonitrile; heterocycles, such as tetrahydrofuran; dialkyl ethers, e.g., diisopropyl ether, 2-methoxyethyl ether, and diethylene ether; an acid, e.g., acetic acid, trifluoroacetic acid, and propionic acid; aqueous solvents, such as water; ionic liquids; and chlorinated solvents, such as methylenechloride. A combination of solvents may also be used. More preferably, the solvent is acetic acid or 2-propanol.

The temperature used in Step (i) is preferably from about 0° C. to about 70° C. More preferably, the temperature is from about 10° C. to about 50° C.; and most preferably from about 10° C. to about 30° C.

The salt having Formula (VI) is preferably 5-[(R)-2-(5,6-diethyl-indan-2-ylamino)-1-hydroxy-ethyl]-8-hydroxy-(1H)-quinolin-2-one benzoate.

In Step (j) the salt having Formula (VI) is treated with an acid in the presence of a solvent to form a salt having Formula (VII)

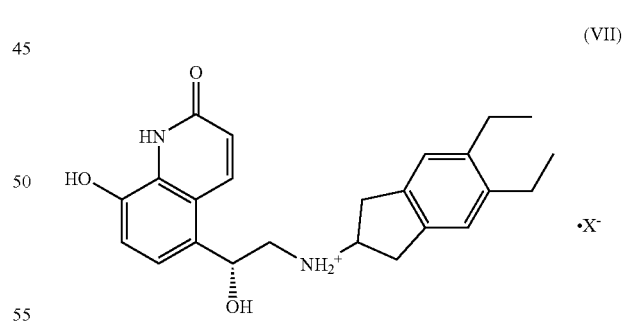

(VII)

wherein X— is an anion. The anion corresponds to the acid used in Step (j). The acid used in Step (j) is preferably a carboxylic acid, such as benzoic acid, maleic acid, succinic acid, fumaric acid, or tartaric acid. Most preferably, the acid used in Step (j) is maleic acid.

The salt having Formula (VII) is preferably 5-[(R)-2-(5,6-diethyl-indan-2-ylamino)-1-hydroxy-ethyl]-8-hydroxy-(1H)-quinolin-2-one maleate having Formula (XXIII):

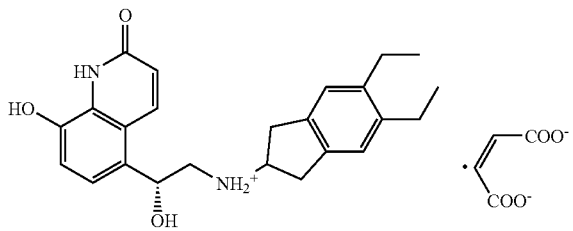

(XXIII)

The solvent used in Step (j) is preferably selected from an alkyl acetate, e.g., $C_1$-$C_6$-alkyl acetates, such as ethyl acetate, isopropyl acetate and butyl acetate; alcohols, e.g. $C_1$-$C_6$-alkyl alcohols, such as methanol, ethanol, propanol, isopropanol, butanol and pentanol; dimethylformamide; aromatic hydrocarbons, such as toluene and benzene; dialkyl ketones, e.g. acetone and methyl isobutyl ketone; acetonitrile; heterocycles, such as tetrahydrofuran; dialkyl ethers, e.g., diisopropyl ether, 2-methoxyethyl ether and diethylene ether; an acid such as acetic acid and propionic acid; aqueous solvents, such as water; ionic liquids; and chlorinated solvents, such as methylenechloride. A combination of solvents may also be used. More preferably, the solvent is ethanol.

The temperature used in Step (j) is preferably from about 0° C. to about 70° C. More preferably, the temperature is from about 10° C. to about 60° C.; and most preferably from about 20° C. to about 50° C.

The invention is illustrated by the following Examples.

EXAMPLES

Example 1

Preparation of 5-acetyl-8-hydroxy-(1H)-quinolin-2-one

Aluminium chloride (93.3 g, 700 mmol, 3.5 eq.) is suspended in 1,2-dichlorobenzene (320 mL). The suspension is maintained at 20-25° C. and 8-hydroxy-(1H)-quinolin-2-one (32.24 g, 200 mmol, 1.0 eq.) is added in 5 portions (40 minutes, IT max. 25° C.). Acetic anhydride (21.4 g, 210 mmol, 1.05 eq.) is slowly added (30 minutes, IT max. 20° C.) and the addition funnel is rinsed with a small amount of 1,2-dichlorobenzene. The suspension is stirred for 30 minutes at 20-25° C. HPLC control reveals complete conversion to 8-acetoxy-(1H)-quinolin-2-one. The mixture is heated to IT=80° C. while purging the head-space with a stream of nitrogen. HCl evolution is noticed upon reaching IT=40° C. The reaction mixture is stirred for 1 hour at IT=80° C. HPLC control reveals almost complete conversion to 5-acetyl-8-hydroxy-(1H)-quinolin-2-one (3.1% O-acetyl intermediate, 10.8% ortho-isomer). The reaction mixture is poured hot (80° C.) over water (800 mL). Water (100 mL) is added in the reaction vessel and brought to reflux temperature. After 15 minutes at reflux temperature, the suspension is added to the previous quench suspension. The mixture is maintained for 15 minutes at IT=80° C. and then hot filtered. The yellow product is rinsed with water (2×200 mL, 50° C.), rinsed with acetone (50 mL) and then dried overnight under vacuum at 70° C. Yield: 33.32 g (82.0%). Purity: 95-97%.

Example 2

Preparation and purification of 5-acetyl-8-hydroxy-(1H)-quinolin-2-one

8-Hydroxy-(1H)-quinolin-2-one (32.24 g, 200 mmol, 1.0 eq) is suspended in 1,2-dichloro benzene (300 mL). The suspension is maintained at 20-25° C. and aluminium chloride (93.3 g, 700 mmol, 3.5 eq.) is added in portions (30 minutes, IT max. 25 IC). Acetic anhydride (21.4 g, 210 mmol, 1.05 eq.) is slowly added (30 minutes, IT max. 20° C.) and the addition funnel is rinsed with a small amount of 1,2-dichlorobenzene. The suspension is stirred for 30 minutes at 20-25° C. HPLC control reveals complete conversion to 8-acetoxy-(1H)-quinolin-2-one. The mixture is heated to IT=80 IC while purging the head-space with a stream of nitrogen. HCl evolution is noticed upon reaching IT=40° C. The reaction mixture is stirred for 1 hour at IT=80° C. HPLC control reveals almost complete conversion to 5-acetyl-8-hydroxy-(1H)-quinolin-2-one (1.8% O-acetyl intermediate, 7.2% ortho-isomer). The reaction mixture is heated to IT=90° C. and poured hot (90 ° C.) over water (645 mL). Water (100 mL) is added in the reaction vessel and brought to reflux temperature. After 15 minutes at reflux temperature, the suspension is added to the previous quench suspension. The mixture is maintained for 15 minutes at IT=80° C. and is hot filtered. The yellow product is rinsed with water (2×200 mL, 50° C.). The crude product (70.1 g) is suspended in acetic acid (495 mL) and the suspension is heated to reflux temperature for 30 minutes. The suspension is cooled down to IT=20° C. and then filtered. The product is washed with acetic acid/water 1/1 (60 mL) and washed with water (5×100 mL) before being dried at 70° C. under vacuum to yield the title compound in 75% yield (31.48 g) and with 99.9% purity.

Example 3

Preparation of 5-acetyl-8-hydroxy-(1H)-quinolin-2-one

5-Acetyl-8-hydroxy-(1H)-quinolin-2-one is prepared according to the procedure set forth in Example 1 except that 3 eq. of aluminium chloride is used instead of 3.5 eq. of aluminium chloride. The yield of the title compound is approximately 84%.

Example 4

Preparation of 5-acetyl-8-hydroxy-(1H)-quinolin-2-one from 8-acetoxy-(1H)-quinolin-2-one 8-Acetoxy-(1H)-quinolin-2-one (6.1 g, 30 mmol, 1.0 eq.) is suspended in 1,2-dichlorobenzene (80 mL). The suspension is warmed to 80° C. and aluminium chloride (12.0 g, 90 mmol, 3.0 eq.) is added in portions. The reaction is stirred for 1 hour at IT=80° C. HPLC control reveals almost complete conversion to 5-acetyl-8-hydroxy-(1H)-quinolin-2one. The reaction mixture is poured hot (80° C.) over water (100 mL). Water (30 mL) is added in the reaction vessel and then brought to reflux temperature. After 15 minutes at reflux temperature, the suspension is added to the previous quench suspension. The mixture is maintained for 15 minutes at IT=80° C. and then hot filtered. The yellow product is rinsed with water (2×50 mL, 50° C.) and then dried overnight under vacuum at 80° C. Yield: 4.32 g (79.0%). Purity: 95%.

Example 5

Preparation of 5-acetyl-8-benzyloxy-1H)-quinolin-2-one

Crude 5-acetyl-8-hydroxy-(1H)-quinolin-2-one (8.13 g, 40 mmol, 1.0 eq.) is added to N—N,diisopropylethylamine (6.46 g, 50 mmol, 1.25 eq.) and acetone (64 mL). The suspension is heated to reflux temperature and water is added (8.2 mL). Benzylbromide (7.52 g, 44 mmol, 1.10 eq.) is added drop-wise and the reaction is maintained for 6-7 hours at reflux temperature until all starting material has reacted. Water (20 mL) is added at IT=58° C. and the mixture is cooled down to 20-25° C. The product is filtered, washed with acetone/water (1/1, 2×8.5 mL) and then with water (4×8 mL). The crude product is dried overnight under vacuum (60° C.). Yield: 10.77 g (91.7%). Purity of the crude product: 99.5%. The product may be recrystallized from acetone/water.

Example 6

Preparation of 1-(α-chloroacetyl)-8-(phenyl-methoxy)-(1H)-quinolin-2-one

A 3 L, 4-necked flask equipped with a mechanical stirrer, thermometer, addition funnel and refluxing condenser is charged with 40 g 8-(phenylmethoxy)-5-acetyl-(1H)-quinolin-2-one and 800 mL acetic acid under an atmosphere of nitrogen. To this yellow solution is added 94.93 g benzyltrimethylammoniumdichloroiodate and 400 mL acetic acid. The resulting suspension is heated under stirring to an internal temperature of 65-70° C. The mixture is stirred at this internal temperature until an in-process control shows complete conversion to 5-chloroacetyll-8-phenylmethoxy-(1H)-quinolin-2-one. Then the mixture is cooled to an internal temperature of 40-45° C. Within 30-60 minutes, 600 mL water is added. The resulting suspension is stirred at room temperature for 30-60 minutes and then filtered. The solid residue is washed with 200 mL water in several portions and then added to 2000 L ethyl acetate in a 3 L, 4-necked flask equipped with a mechanical stirrer, thermometer and refluxing condenser. This mixture is heated to reflux and refluxed for 15 minutes. The mixture is cooled to an internal temperature of 0-2° C. and stirred at this internal temperature for 2 hours. The mixture is filtered and washed with 250 mL water in several portions, and dried overnight in a vacuum drier at 60° C. to give the title compound with a yield of 39.64 g.

Example 7

Preparation of 8-(phenylmethoxy)-5-((R)-2-chloro-1-hydroxy-ethyl)-(1H)-quinolin-2-one A dry 3 L, 4-necked flask equipped with a mechanical stirrer, thermometer, addition funnel and refluxing condenser is charged with 50 g 8-(phenylmethoxy)-5-(α-chloroacetyl)-(1H)-quinolin-2-one and 600 mL dry THF under $N_2$. Then 15 mL of a 1 molar solution of (R)-tetrahydro-1-methyl-3,3-diphenyl-(1H,3H)-pyrrolo[1,2-c][1,3,2]-oxazaborole in toluene is added. The mixture is cooled to an internal temperature of 0-2° C. and while maintaining an internal temperature of 0-2° C., 153 mL of a 1 molar solution of $BH_3$ in THF is added over 1-2 hours. The reaction is stirred for another hour at an internal temperature of 0-2° C. and then quenched by addition of 65 mL methanol. The resulting solution is warmed to 25° C. and concentrated to a volume of 250 mL (50° C./200 mbar). To this concentrate is added a mixture of 713 mL water and 37 g HCl 37%. During the addition 8-(phenylmethoxy)-5-((R)-2-chloro-1-hydroxy-ethyl)-(1-H)-quinolin-2-one precipitates as a nearly colourless precipitation. The resulting suspension is stirred for 30 minutes at 25° C., filtrated and washed with 220 mL water in several portions. Drying in a vacuum drier at 50° C. for 12 hours results in 47.41 g of 8-(phenylmethoxy)-5-((R)-2-chloro-1-hydroxy-ethyl)-(1H)-quinolin-2-one as a slightly yellowish powder.

Example 8

Preparation of 8-(phenylmethoxy)-5-(R)-oxiranyl-(1H)-Quinolin-2-one

A 3 L, 4-necked flask equipped with a mechanical stirrer, thermometer, addition funnel and refluxing condenser is charged with 50 g 8-(phenylmethoxy)-5-((R)-2-chloro-1-hydroxy-ethyl)-(1H)-quinolin-2-one, 52.42 g potassium carbonate, 2500 mL acetone and 25 mL water. The mixture is heated under stirring to reflux. Refluxing is maintained for 5-10 hours until an in-process control shows complete conversion of 8-phenylmethoxy-5-((R)-2-chloro-1-hydroxy-ethyl)-(1H)-quinolin-2-one to 8-phenylmethoxy-5-(R)-oxiranyl-(1H)-quinolin-2-one. When the reaction is complete, the hot (45-50° C.) reaction mixture is filtered to remove the inorganic salts. The residue is washed with several portions of acetone, and the combined mother liquor and acetone washings are concentrated to a volume of 450 mL. To the resulting suspension is added 235 mL heptane at 25° C. and then the suspension is cooled to an internal temperature of 0-2° C. and stirred at this temperature for 2-3 hours. Filtration and washing results in a crude 8-phenylmethoxy-5-(R)-oxiranyl-(1H)-quinolin-2-one which is re-crystallized from toluene. This results in 36.7 g 8-(phenylmethoxy)-5-(R)-oxiranyl-(1H)-quinolin-2-one as nearly colourless solid.

Example 9

Preparation of 5-[(R)-2-(5,6-diethyl-indan-2-ylamino)-1-hydroxy-ethyl]-8-phenylmethoxy-(1H)-quinolin-2-one benzoate A 1 L, 4-necked flask equipped with a mechanical stirrer, thermometer, addition funnel and refluxing condenser is charged with 30.89 grams of 2-amino-5,6-diethylindan and diethylene glycol dimethyl ether. To this solution is added 36.4 grams of 8-phenyl-methoxy-5-(R)-oxiranyl-1H-quinolin-2-one. The resulting suspension is heated to a temperature of 110° C. and stirred at this temperature for 15 hours. The resulting brown solution is cooled to 70° C. At 70° C., 210 mL of ethanol is added followed by a solution of 30.3 grams of benzoic acid in 140 mL of ethanol. The solution is cooled to 45-50° C. and seeded. The suspension is cooled to 0-5° C. The crude 8-phenylmethoxy-5-[(R)-2-(5,6-diethyl-indan-2-ylamino)-1-hydroxy-ethyl]-1H-quinolin-2-one benzoate is isolated by filtration and washed with 150 mL of ethanol in three portions. The wet filter cake is purified by re-crystallization from 1400 mL of ethanol, which gives 50.08 g pure 8-phenylmethoxy-5-[(R)-2-(5,6-diethyl-indan-2-ylamino)-1-hydroxy-ethyl]-1H-quinolin-2-one benzoate as a white crystalline powder.

Example 10

Preparation of 5-[(R)-2-(5,6-diethyl-indan-2-ylamino)-1-hydroxy-ethyl]-8-hydroxy-1H-quinolin-2-one maleate A 1 L hydrogenation vessel is charged with 40 grams of 8-phenylmethloxy-5-[(R)-2-(5,6-diethyl-indan-2-ylamino)-1-hydroxy-ethyl]-1H-quinolin-2-one benzoate and 400 mL of acetic acid. Palladium on charcoal 5% (5.44 g) is added and the reaction mass is hydrogenated for 2-8 hours until complete conversion to 5-[(R)-2-(5,6-diethyl-indan-2-ylamino)-1-hydroxy-ethyl]-8-hydroxy-1H-quinolin-2-one. The mixture is filtered over a pad of filter-aid. The filtrate is concentrated at 50-60° C. under vacuum (100 mbar) to a volume of 70-90 mL. This residue is dissolved in 400 mL of ethanol and heated to 50-60° C. A solution of 11.6 g maleic acid in 24 mL ethanol is added and the resulting clear solution is seeded at an internal temperature of 50° C. with a suspension of 350 mg micronised 5-[(R)-2-(5,6-diethyl-indan-2-ylamino)-1-hydroxy-ethyl]-8-hydroxy-1H-quinolin-2-one in 20 mL isopropanol. The product is crystallized by slow cooling to 0-5° C. Filtration and washing with 50 mL of ethanol followed by 25 mL of isopropanol provides 65 g crude 5-[(R)-2-(5,6-diethyl-indan-2-ylamino)-1-hydroxy-ethyl]-8-hydroxy-1H-quinolin-2-one maleate which is further purified by crystallization from 1.36 L of ethanol. This gives 24.3 g pure 5-[(R)-2-(5,6-diethyl-indan-2-ylamino)-1-hydroxy-ethyl]-8-hydroxy-1H-quinolin-2-one maleate as a white crystalline powder.

Example 11

Purity and Yield of Different Salts of 5-[(R)-2-(5,6-diethyl-indan-2-ylamino)-1-hydroxy-ethyl]-8-substituted oxy-(1H)-quinolin-2-one A 1 L, 4-necked flask equipped with a mechanical stirrer, thermometer, addition funnel and refluxing condenser is charged with 30.89 grams of 2-amino-5,6-diethylindan and diethylene glycol dimethyl ether. To this solution is added 36.4 grams of 8-phenyl-methoxy-5-(R)-oxiranyl-1H-quinolin-2-one. The resulting suspension is heated to a temperature of 110° C. and stirred at this temperature for 15 hours. The resulting brown solution is cooled to 70° C.

The reaction is conducted as follows:

As determined by HPLC, the reaction mixture contains 68.7% of a compound having Formula (II), 7.8% of a compound having Formula (III), and 12.4% of a compound having Formula (IV). The reaction mixture is split in equal portions and each portion is individually treated with an acid selected from benzoic acid, maleic acid, succinic acid, fumaric acid, tartaric acid and hydrochloric acid. The results are summarized in Table 1 as follows:

TABLE 1

| Salt | Purity [% (Area)] | Yield [%] |
|---|---|---|
| Benzoate | 96 | 60 |
| Maleate | 98 | 28 |
| Fumarate | 97 | 48 |
| Succinate | 98 | 30 |
| Tartrate | 98 | 25 |
| Hydrochloride | 87 | 25 |

As set forth in Table 1, the percent yield is based on the amount of 8-substituted oxy-5-(R)-oxiranyl-(1H)-quinolin-2-one, and the purity is based on the salt having Formula (II) and is determined by HPLC.

The invention claimed is:

1. A process for preparing 5-(α-haloacetyl)-8-substituted oxy-(1H)-quinolin-2-ones comprising:
   (a) reacting
      (i) 8-hydroxy-(1H)-quinolin-2-one with an acylating agent and a Lewis acid to form 5-acetyl-8-hydroxy-(1H)-quinolin-2-one; or
      (ii) 8-hydroxy-(1H)-quinolin-2-one with an acylating agent to form 8-acetoxy-(1H)-quinolin-2-one, and treating, in-situ, the 8-acetoxy-(1H)-quinolin-2-one with a Lewis acid to form 5-acetyl-8-hydroxy-(1H)-quinolin-2-one;
   (b) reacting the 5-acetyl-8-hydroxy-(1H)-quinolin-2-one prepared in Step (a) with a compound having the Formula RL in the presence of a base and a solvent to form 5-acetyl-8-substituted oxy-(1H)-quinolin-2-one, wherein R is a protecting group and L is a leaving group; and
   (c) reacting the 5-acetyl-8-substituted oxy-(1H)-quinolin-2-one with a halogenating agent in the presence of a solvent to form a 5-(α-haloacetyl)-8-substituted oxy-(1H)-quinolin-2-one.

2. A process according to claim 1 is present in an amount of from 1 molar equivalents to 1.5 molar equivalents, based on the molar equivalents of 8-hydroxy-(1H)-quinolin-2-one.

3. A process according to claim 1, wherein the Lewis acid is present in an amount of from 3 molar equivalents to 5 molar equivalents, based on the molar equivalents of 8-hydroxy-(1H)-quinolin-2-one or on the molar equivalents of 8-acetoxy-(1H)-quinolin-2-one.

4. A process according to claim 1, wherein Step (a) is conducted in the presence of an alkaline halide selected from the group consisting of sodium chloride, sodium bromide, lithium chloride and lithium bromide.

5. A process according to claim 1, wherein the compound having the Formula RL is selected from the group consisting of α-methylbenzyl bromide, methyl chloride, benzylchloride and benzylbromide.

6. A process according to claim 1, wherein the 5-acetyl-8-substituted oxy-(1H)-quinolin-2-one is 5-acetyl-8-benzyloxy-(1H)-quinolin-2-one.

7. A process according to claim 1, wherein the halogenating agent is selected from the group consisting of sodium bromate and hydrobromic acid, bromine, N-bromosuccinimide, N-chlorosuccinimide, iodine, chlorine, sulfuryl chloride, benzyltrimethylammoniumdichloro-iodate, copper chloride, pyridinium tribromide, tetraalkylammonium tribromide, iodine chloride, hydrochloric acid and an oxidating agent and combinations thereof.

8. A process according to claim 7, wherein the halogenating agent is benzyltrimethyl-ammoniumdichloroiodate.

9. A process according to claim 1, wherein the 5-(α-haloacetyl)-8-substituted oxy-(1H)-quinolin-2-one is 5-(α-chloroacetyl)-8-benzyloxy-(1H)-quinolin-2-one.

10. A process according to claim 1, wherein in Step (a) the solvent is selected from the group consisting of methylenechloride, 1,2-ethylene dichloride, chlorobenzene, o-dichloro-benzene, aliphatic $C_6.C_{12}$-hydrocarbons and combinations thereof; in Step (b) the solvent is selected from the group consisting of acetone, methyl isobutyl ketone, tetrahydrofuran, diisopropyl ether, 2-methoxyethyl ether, diethylene ether, methylenechloride, water and combinations thereof; and in Step (c) the solvent is selected from the group consisting of acetic acid, trifluoroacetic acid propionic acid; ethyl acetate, isopropyl acetate, butyl acetate, toluene, benzene, tetrahydrofuran, diisopropyl ether, 2-methoxyethyl ether, diethylene ether, methylenechloride and combinations thereof.

11. A process according to claim 1, wherein in Step (a) the temperature is from 0° C. to 160° C.; in Step (b) the temperature is from 20° C. to 90° C.; and in Step (c) the temperature is from about 10° C. to about 160° C.

12. A process for preparing 5-[(R)-2-(5,6-diethyl-indan-2-ylamino)-1-hydroxy-ethyl]-8-hydroxy-(1H)-quinolinone-2-one salts comprising:
   (a) reacting
      (i) 8-hydroxy-(1H)-quinolin-2-one with an acylating agent and a Lewis acid to form 5-acetyl-8-hydroxy-(1H)-quinolin-2-one; or (ii) 8-hydroxy-(1H)-quinolin-2-one with an acylating agent to form 8-acetoxy-(1H)-quinolin-2-one, and treating, in-situ, the 8-acetoxy-(1H)-quinolin-2-one with a Lewis acid to form 5-acetyl-8-hydroxy-(1H)-quinolin-2-one;

(b) reacting the 5-acetyl-8-hydroxy-(1H)-quinolin-2-one prepared in Step (i) with a compound having the Formula RL in the presence of a base and a solvent to form 5-acetyl-8-substituted oxy-(1H)-quinolin-2-one, wherein R is a protecting group and L is a leaving group;

(c) reacting the 5-acetyl-8-substituted oxy-(1H)-quinolin-2-one with a halogenating agent in the presence of a solvent to form a 5-(α-haloacetyl)-8-substituted oxy-(1H)-quinolin-2-one;

(d) reacting an 5-(α-haloacetyl)-8-substituted oxy-(1H)-quinolin-2-one with a reducing agent in the presence of a chiral catalyst to form 8-(substituted oxy)-5-((R)-2-halo-1-hydroxy-ethyl)-(1H)-quinolin-2-one;

(e) treating the 8-(substituted oxy)-5-((R)-2-halo-1-hydroxy-ethyl)-(1H)-quinolin-2-one with a base in the presence of a solvent to form 8-(substituted oxy)-5-(R)-oxiranyl-(1H)-quinolin-2-one;

(f) reacting the 8-substituted oxy-5-(R)-oxiranyl-(1H)-quinolin-2-one having Formula (I)

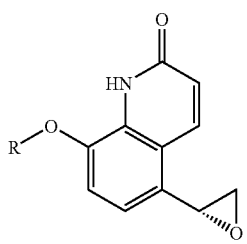

(I)

with 2-amino-(5-6-diethyl)-indan to form a reaction mixture containing compounds having Formulae (II), (III) and (IV)

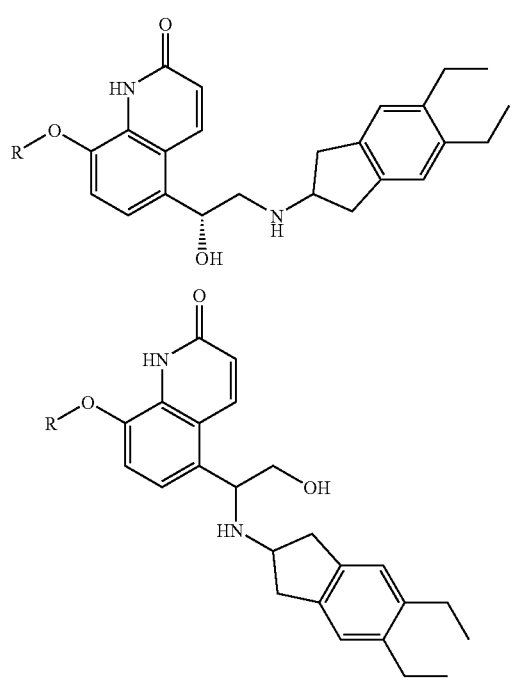

(II)

(III)

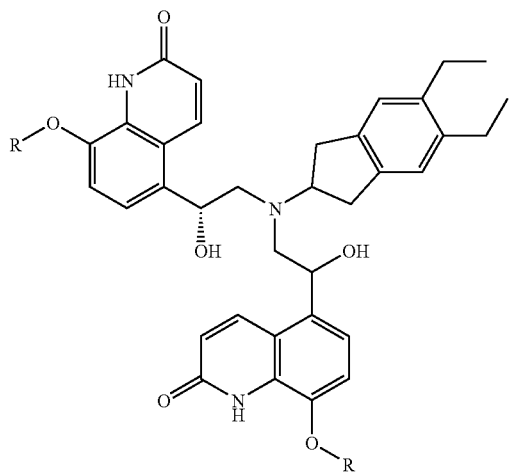

(IV)

wherein R is a protecting group;

(g) treating the reaction mixture prepared in Step (i) with an acid in the presence of a solvent to form a corresponding salt;

(h) isolating and crystallizing a salt having Formula (V)

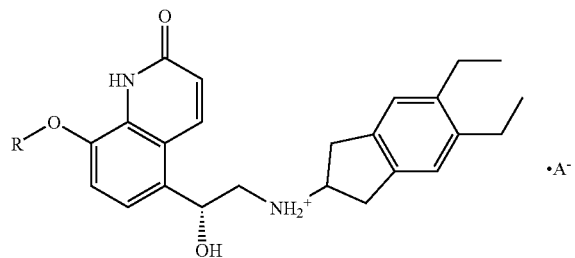

(V)

wherein R is a protecting group and A⁻ is an anion;

(i) removing the protecting group from the salt having Formula (V) in the presence of a solvent to form a salt having Formula (VI):

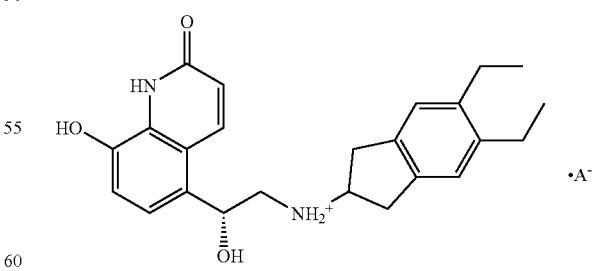

(VI)

wherein A⁻ is an anion; and (j) treating the salt having Formula (VI) with an acid in the presence of a solvent to form 5-[(R)-2-(5,6-diethyl-indan-2-ylamino)-1-hydroxy-ethyl]-8-hydroxy-(1H)-quinolin-2-one salt having Formula (VII)

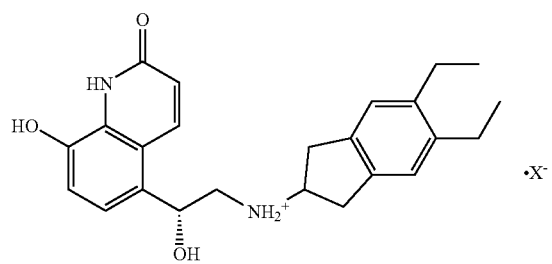 (VII)

wherein X⁻ is an anion.

13. A process according to claim 2, wherein the acylating agent is acetic anhydride or acetyl chloride.

14. A process according to claim 4, wherein the Lewis acid is selected from the group consisting of boron trifluoride, aluminium chloride or titanium tetrachloride.

15. A process according to claim 4, wherein Step (a) is conducted in the presence of an ionic liquid selected from the group consisting of an imidazolium salt, pyridium salt, ammonium salt, phosphonium salt and sulphonium salt.

* * * * *

UNITED STATES PATENT AND TRADEMARK OFFICE
CERTIFICATE OF CORRECTION

| | | |
|---|---|---|
| PATENT NO. | : 7,605,267 B2 | Page 1 of 1 |
| APPLICATION NO. | : 10/550621 | |
| DATED | : October 20, 2009 | |
| INVENTOR(S) | : Olivier Lohse et al. | |

It is certified that error appears in the above-identified patent and that said Letters Patent is hereby corrected as shown below:

On the Title page,

Item [*] Notice:   Subject to any disclaimer, the term of this patent is extended or adjusted under 35 U.S.C. 154(b) by 540 days.

Delete the phrase "by 540 days" and insert -- by 922 days --

Signed and Sealed this

Twenty-fourth Day of August, 2010

David J. Kappos
*Director of the United States Patent and Trademark Office*